United States Patent
Naggi et al.

(10) Patent No.: US 6,770,148 B1
(45) Date of Patent: Aug. 3, 2004

(54) PERITONEAL DIALYSIS SOLUTION CONTAINING MODIFIED ICODEXTRINS

(75) Inventors: Annamaria Naggi, Legnano (IT); Enrico Petrella, Mirandola (IT); Giangiacomo Torri, Milan (IT); Benito Casu, Milan (IT)

(73) Assignee: Baxter International Inc., Deerfield, IL (US)

( * ) Notice: Subject to any disclaimer, the term of this patent is extended or adjusted under 35 U.S.C. 154(b) by 605 days.

(21) Appl. No.: 09/206,063

(22) Filed: Dec. 4, 1998

(51) Int. Cl.[7] .................. C08B 30/00; C08B 31/00
(52) U.S. Cl. ................. 127/71; 536/45; 514/60; 514/54
(58) Field of Search ................. 514/60, 54; 127/71; 536/45

(56) References Cited

U.S. PATENT DOCUMENTS

| | | | | |
|---|---|---|---|---|
| 3,974,034 A | * | 8/1976 | Horn et al. | 435/99 |
| 4,339,433 A | | 7/1982 | Kartinos et al. | |
| 4,761,237 A | | 8/1988 | Alexander et al. | |
| 4,879,280 A | | 11/1989 | Seyffart et al. | 514/53 |
| 4,886,789 A | * | 12/1989 | Milner | 514/60 |

FOREIGN PATENT DOCUMENTS

| | | |
|---|---|---|
| EP | 0 076 355 A3 | 2/1982 |
| EP | 0 115 911 A1 | 1/1984 |
| EP | 0 153 164 A2 | 2/1985 |
| EP | 0 153 164 B1 | 2/1985 |
| EP | 0 207 676 A3 | 6/1986 |
| EP | 0 218 900 B1 | 9/1986 |
| EP | 0612528 * 2/1994 | .......... A61K/33/14 |
| JP | 60-166378 | 2/1984 |
| WO | WO 97/06810 | 8/1996 |

OTHER PUBLICATIONS

Eliasson, Carbohydrates in Food, Chapter 4, "Cell Wall Polysaccharide Structural, Chemical and Analytical Aspects," pp. 191, 195 (1996).*

Solomons, Organic Chemistry ($2^{nd}$ ed.), John Wiley and Sons, New York, p. 890 (1980).*

* cited by examiner

*Primary Examiner*—James O. Wilson
*Assistant Examiner*—Howard V. Owens, Jr.
(74) *Attorney, Agent, or Firm*—Paula J. F. Kelly; Joseph P. Reagen; Bell, Boyd & Lloyd LLC

(57) ABSTRACT

The present invention provides a peritoneal dialysis solution that contains heat stable osmotic agents such as D-glucitols, gluconic acids and alkylglycosides produced the reduction, oxidation or glycosylation of icodextrins respectively. As a result, osmotic agents that are stable under autoclaving or heat sterilization conditions are provided which reduces the amount of bioincompatible materials in the sterilized peritoneal dialysis solutions. Methods of preparing the D-glucitols, gluconic acids and alkylglycosides are disclosed.

6 Claims, 2 Drawing Sheets

PERITONEAL DIALYSIS SOLUTION CONTAINING MODIFIED ICODEXTRINS

BACKGROUND OF THE INVENTION

The present invention relates generally to peritoneal dialysis and solutions for the same. More specifically, the present invention relates to the use of modified icodextrins in peritoneal dialysis solutions as an osmotic agent and as an alternative to the use of glucose as an osmotic agent. The present invention also relates to methods of preparing peritoneal dialysis solutions that are stable under autoclaving conditions.

Dialysis provides a method for supplementing or replacing renal function in certain patients. Principally, hemodialysis and peritoneal dialysis are the two methods that are currently utilized.

In hemodialysis, the patient's blood is passed through an artificial kidney dialysis machine. A membrane in the machine acts as an artificial kidney for cleansing the blood. Because it is an extracorporeal treatment that requires special machinery, hemodialysis is fraught with certain inherent disadvantages such as the availability of dialysis machines and the possibility of infection and contamination.

To overcome the disadvantages associated with hemodialysis, peritoneal dialysis was developed. Peritoneal dialysis utilizes the patient's own peritoneum as a semi-permeable membrane. The peritoneum is a membranous lining of the abdominopelvic walls of the body. The peritoneum is capable of acting as a natural semi-permeable membrane because of its large number of blood vessels and capillaries.

In operation, a peritoneal dialysis solution is introduced into the peritoneal cavity utilizing a catheter. After a sufficient period of time, an exchange of solutes between the dialysate and blood is achieved. Fluid removal is achieved by providing a suitable osmotic gradient from the dialysate to the blood to permit water outflow from the blood. This allows the proper acid-base, electrolyte and fluid balance to be achieved in the blood. After an appropriate dwell period, the dialysis solution or dialysate is drained from the body through a catheter.

Conventional peritoneal dialysis solutions contain glucose as an osmotic agent to maintain the osmotic pressure of the solution higher than the physiological osmotic pressure (about 285 mOsmol/kg). Glucose is a preferred osmotic agent because it provides rapid ultrafiltration rates. However, certain disadvantages have become associated with the use of glucose.

For example, glucose is known to decompose to 5-hydroxymethyl-furfural (5-MHF) in an aqueous solution during autoclaving or steamed sterilization. Smith, et al. *AM. J. Hosp. Pharm.*, 34:205–206 (1977). Because 5-HMF is considered to be harmful for the peritoneum (Henderson, et al., *Blood Purif.*, 7:86–94 (1989)), it would be desirable to have a peritoneal dialysis solution with an osmotic agent as effective as glucose but which does not produce 5-HMF or other harmful decomposition products during autoclaving or sterilization. In short, a substitute osmotic agent for glucose is needed.

One family of compounds capable of serving as osmotic agents in peritoneal dialysis solutions is icodextrins, including maltodextrins. However, while these compounds are suitable for use as osmotic agents, they are also known to degrade during heat sterilization to aldonic acids and formaldehyde. Because the presence of formaldehyde in peritoneal dialysis solutions is inappropriate due to its poor biocompatibility, the use of icodextrins, including maltodextrins as a substitute for glucose as an osmotic agent is unsatisfactory.

Accordingly, there is a need for an improved peritoneal dialysis solution which utilizes an osmotic agent other than glucose and which is stable under autoclaving or steam sterilization conditions.

SUMMARY OF THE INVENTION

The present invention provides a solution to the aforenoted need by providing a sterilized peritoneal dialysis solution comprising a glucose polymer linked predominately by α-1,4 bonds. The term "predominately" is used because it is anticipated that within polymer molecules, other bonds such as α-1,6 bonds will be present as well, but in lesser amounts. Accordingly, as used herein, the term "predominately" means at least 85%. Thus, a glucose polymer linked predominately by α-1,4 bonds includes at least 85%, by number, α-1,4 bonds.

In an embodiment, the glucose polymer linked predominately by α-1,4 bonds is selected from the group consisting of D-glucitol having the formula

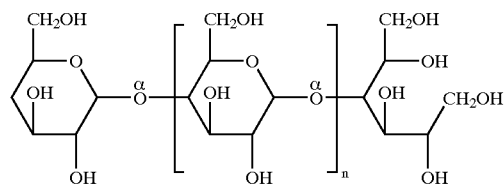

gluconic acid having the formula

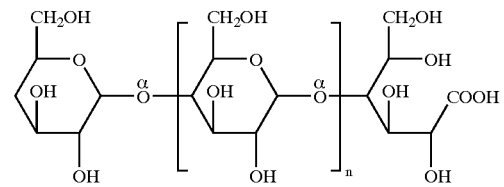

and alkylglycoside having the formula

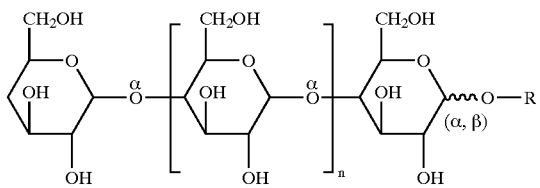

wherein R is selected from the group consisting of $CH_3$, $CH_3CH_2$ and $(CH_2OH)_2CH$, $CH_2(OH)CH(OH)CH_2$, and $(CH_2OH)(CHOHCH_2OH)CH$.

In an embodiment, the glucose polymers, linked predominately by α-1,4 linkages, of the peritoneal dialysis solution may include up to 10% of other linkages including, but not limited to, α-1,6 linkages.

In an embodiment, the peritoneal dialysis solution of the present invention is substantially free of formaldehyde.

In an embodiment, the peritoneal dialysis solution of the present invention is substantially free of furfurals.

In an embodiment, starch utilized as the osmotic agent is substantially free of terminal aldehyde groups.

In an embodiment, the present invention provides a method of preparing a stabilized osmotic agent of a peritoneal dialysis solution comprising the steps of providing a solution of starch dissolved in water and adding $NaBH_4$ to the solution of partially hydrolyzed starch to reduce the starch.

In an embodiment, the method of the present invention further comprises the step of purifying the reduced starch solution by passing the reduced starch solution through an anionic exchange resin.

In an embodiment, the dissolving and adding steps of the method of the present invention are carried out at room temperature.

In an embodiment, the method of the present invention further comprises the step of allowing the solution to scan for approximately 10 hours after the $NaBH_4$ is added to the starch solution to reduce the starch.

In an embodiment, the starch of the present invention is maltodextrin.

In an embodiment, the method of the present invention reduces maltodextrin to D-glucitol linked predominately by α-1,4 bonds and having the formula

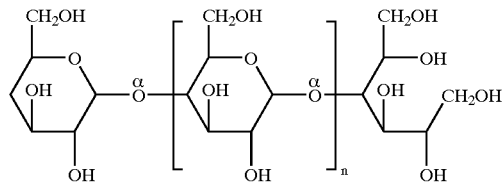

In an embodiment, the present invention provides a method for preparing a stabilized osmotic agent of a peritoneal dialysis solution which comprises the steps of providing a solution of starch dissolved in water, providing a solution of NaOCl, and adding the NaOCl solution to the starch solution to oxidize the starch.

In an embodiment, the method of the present invention further comprises the step of purifying the oxidized starch solution by passing the oxidized starch solution through a gel permeation chromatograph.

In an embodiment, the oxidation of the starch is carried out at room temperature.

In an embodiment, the combined solutions are allowed to stand for approximately 2 hours.

In an embodiment, the starch is maltodextrin.

In an embodiment, the method of the present invention oxidizes the maltodextrin to a gluconic acid linked predominately by α-1,4 bonds and having the formula

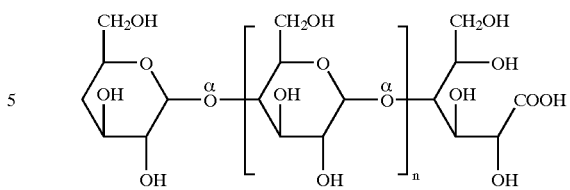

In an embodiment, the maltodextrin can be oxidized electrochemically.

In an embodiment, the present invention provides a method of preparing a stabilized osmotic agent for a peritoneal dialysis solution which comprises the steps of dissolving the starch in an acid and an alcohol selected from the group consisting of methanol, butanol, glycerol or other alcohols.

In an embodiment, the method further comprises the step of stirring the starch, alcohol and acid for 2–16 hours.

In an embodiment, the method further comprises the step of stirring the starch, alcohol and acid at a temperature of about 100° C.

In an embodiment, the starch is maltodextrin.

In an embodiment, the acid is hydrochloric acid or other acids such as sulfuric acid.

In an embodiment, the method of the present invention hydrolysizes and alkylates the starch to an alkylglycoside linked predominately by α-1,4 bonds and having the formula

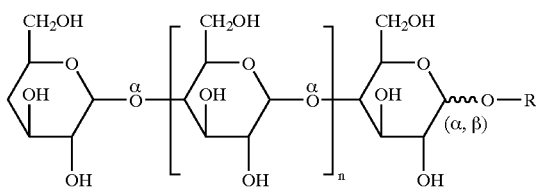

and wherein R is selected from the group consisting of $CH_3$, $CH_3CH_2$ and $(CH_2OH)_2CH$. When hydrolysis is performed on starch pre-treated with periodate, R is the remnant of a glycol-split glucose unit.

It is therefore an advantage of the present invention to provide an improved peritoneal dialysis solution which is stable under autoclaving and steam sterilization conditions.

Another advantage of the present invention is that it provides an improved osmotic agent as an alternative to glucose.

Yet another advantage of the present invention is that it provides improved methods of preparing peritoneal dialysis solutions.

Yet another advantage of the present invention is that it provides improved osmotic agents for peritoneal dialysis solutions which are stable under autoclaving or steam sterilization conditions.

Additional features and advantages of the present invention are described in, and will be apparent from, the detailed description of the presently preferred embodiments and upon reference to the accompanying figures.

DETAILED DESCRIPTION OF THE PRESENTLY PREFERRED EMBODIMENTS

Figure 1:
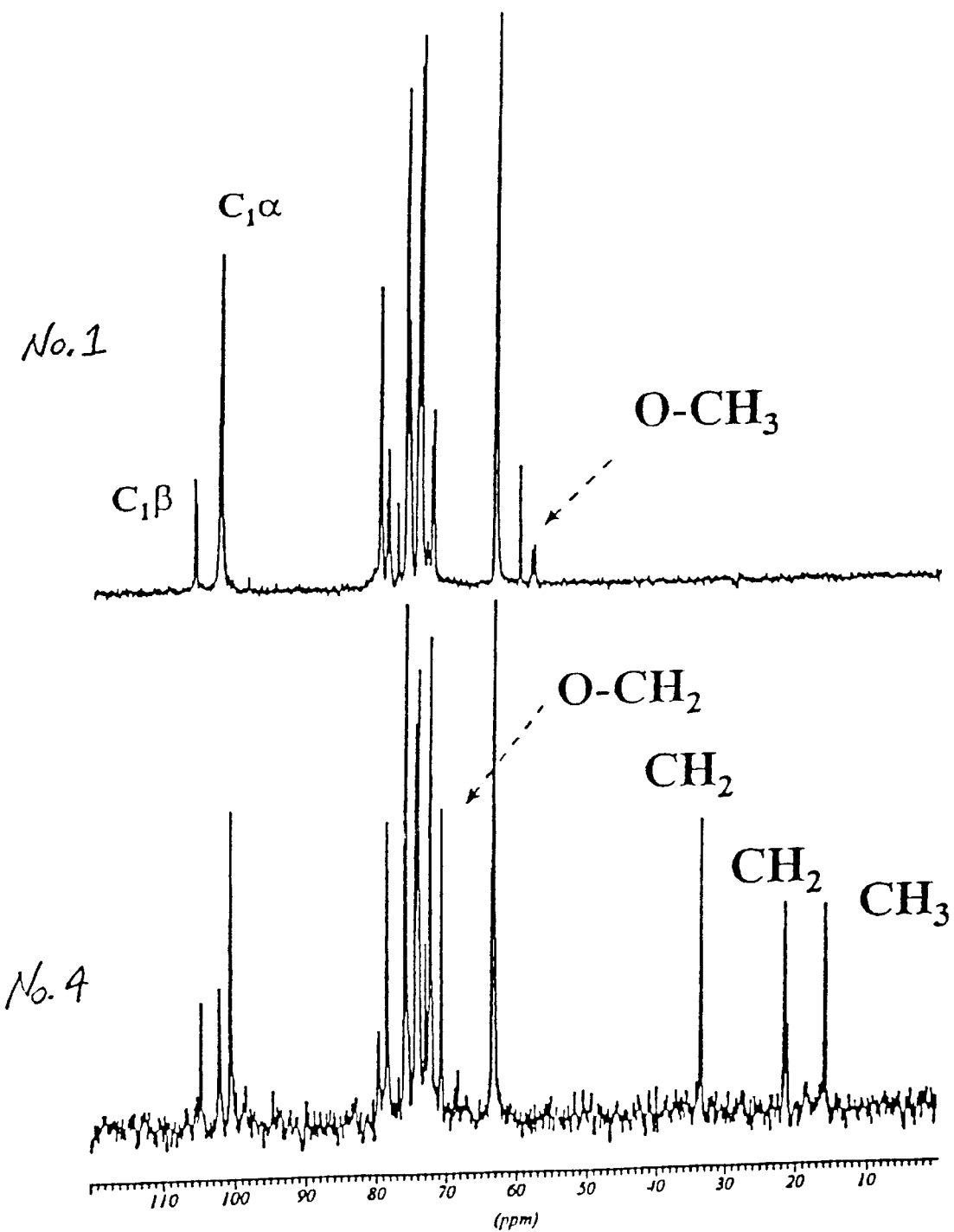
FIG. 1 is a graphical illustration of the $^{13}C$ NMR spectrum of an osmotic agent prepared by glycosylation in accordance with the present invention.

The present invention provides a peritoneal dialysis solution with osmotic agents that are stable under autoclaving and steam sterilization conditions. The stable osmotic agents of the present invention may be prepared by reduction, oxidation or glycosylation. When an icodextrin having reducing-end units are employed, such as maltodextrin, the reduction, oxidation or glycosylation procedures of the present invention transform the icodextrin to corresponding D-glucitols, gluconic acids and alkyglycosides respectively.

EXAMPLE 1

A reduced icodextrin was prepared by starting with 15 grams of maltodextrin dissolved in 20 ml of water. One gram of NaBH$_4$ was added to the solution at room temperature and the solution was allowed to stand for 10 hours. The solution was then purified by passing it through an anionic exchange resin.

Three different maltodextrin starting materials were utilized. A low molecular weight (LMW) having a 3% degree of polymerization (DP) was utilized that contained 1% glucose, 37% maltose, 20% maltotetraose and 42% high molecular weight oligosaccharides. Second, a high molecular weight maltodextrin (HMW1) having a 14% degree of polymerization was utilized and contained 1% glucose, 2% maltose, 4% maltotetraose and 94% high molecular weight oliogosaccharides. Third, a second high molecular weight maltodextrin (HMW2) with a 9% degree of polymerization containing 1% glucose, 3% maltose, 7% maltotetraose and 90% high molecular weight oliogosaccharides was utilized. The products and starting materials were analyzed using $^{13}$C NMR spectroscopy. The signals associated with the reducing end units of the starting materials completely disappeared in the specter of the products. Some depolymerization was observed.

The products were tested for stability under isterilization conditions at neutral pH. A significant reduction of absorbance variation at 284 nm (Δ Abs) after sterilization is observed for the reduced compounds. The reduced compounds from Example 1 are listed as HMW1 red, HMW2 red and LMW red in Table 1.

EXAMPLE 2

Utilizing the three different samples of maltodextrins discussed above with respect to Example 1, oxidation reactions were carried out on each sample by dissolving 15 grams of maltodextrin in 30 ml of water and combining the starch solution with an effective amount of NaOCl in 70 ml of a solution containing sodium hydroxide and having a pH of 8±0.5 at a temperature of 43° C. The combined solutions were allowed to stand for approximately 2 hours and the product solution was purified by gel permeation chromatography. Again, the products were analyzed using $^{13}$C NMR spectroscopy and were tested for stability under sterilization conditions as illustrated in Table 1. While the oxidation products, HMW1 ox HMW2 ox and LMW ox show contrasting results, this is attributed to the high molecular weight oxidized products not being completely purified.

TABLE 1

Absorbance (284 nm) variation after sterilization (121° C. 45 min) of 5% Icodextrin and modified Icodextrin solutions

| CODE | Number of experiments | ΔAbs (pH 6.5–7.5) | ΔAbs (pH 5.5) |
| --- | --- | --- | --- |
| HMW1 | 6 | 0.65 ± 0.30 | 0.59 ± 0.35 |
| HMW1 red | 6 | 0.31 ± 0.10 | 0.20 ± 0.07 |
| HHW1 ox | 2 | 1.83 ± 0.21 | 1.78 ± 0.13 |
| HMW2 | 8 | 1.21 ± 0.71 | 0.62 ± 0.71 |
| HMW2 red | 7 | 0.13 ± 0.09 | 0.09 ± 0.06 |
| HMW2 ox | 4 | 0.76 ± 0.31 | 0.79 ± 0.19 |
| LMW | 8 | 1.96 ± 0.87 | 1.33 ± 0.86 |
| LMW red | 8 | 0.18 ± 0.11 | 0.17 ± 0.07 |
| LMW ox | 3 | 0.01 ± 0.01 | 0.02 ± 0.01 |
| Reference compounds | | | |
| Glucose | 4 | 2.54 ± 0.78 | 2.36 ± 0.96 |
| *Glucose | 2 | 0.98 | |
| *D(+)-Gluconolactone | 1 | 0.01 | |

*Glucose and D(+)-Gluconolactone solutions are 2.5% at pH 7
ΔAbs = difference between absorbance after and before sterilization

EXAMPLE 3

In a third method of preparing stable osmotic agents in accordance with the present invention, icodextrin were glycosylated. The glycosylation reactions were performed using starch as the starting material and alcohol as the alkylating agent. Butanol and glycerol were chosen because of their biocompatibility. The molecular weight of the reaction products depends upon the temperature, time and acid concentration used.

Figure 2:
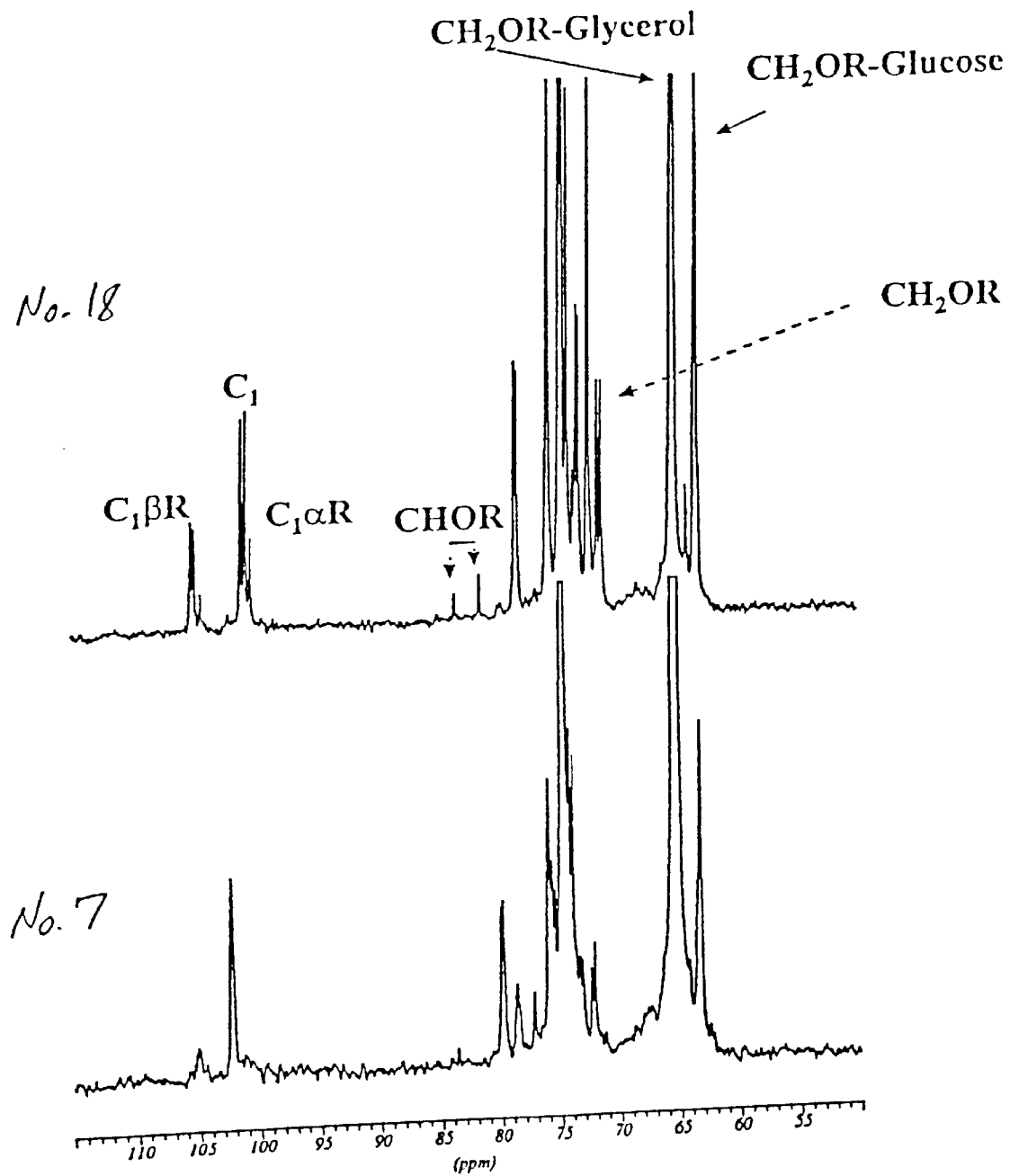
FIG. 2 is a graphical illustration of the $^{13}$C NMR spectrum of an osmotic agent prepared by glycosylation in accordance with the present invention.

The hydrolysis with methanol and butanol were performed by stirring a suspension of 200 mg of starch in 540 mg of alcohol containing 60 mg of acid at a temperature of about 100° C. for approximately 2 hours. The $^{13}$C NMR spectrum of the two products obtained from this reaction with methanol and butanol respectively are shown in FIGS. 1 and 2. Table 2 presents the degree of polymerization (DP) and the percentage of non-substituted reducing ends as a function of the reaction conditions. This data was obtained from the ratio between the appropriate NMR signals ($^1$H NMR for DP values and $^{13}$C NMR for the percentage of nonsubstituted reducing ends).

TABLE 2

Glycosylation reaction with MeOH and ButOH

| Sample No. | Alcohol | Acid M/f | D.P. | % non substituted glucose |
| --- | --- | --- | --- | --- |
| 1 | MeOH | H$_2$SO$_4$ | 4.1 | 8.7 |
| 2 | MeOH | HCl | 5.2 | 11.2 |
| 3 | ButOH | H$_2$SO$_4$ | 1.3 | 41.6 |
| 4 | ButOH | HCl | 1.4 | 13.0 |

EXAMPLE 4

In the case of alcoholysis with glycerol, the reactions were performed using 1 gram of undried starch (humidity 9%) and 2.7 grams of glycerol and stirring the mixture at 100° C. with different amounts of hydrochloric acid for different time periods. Glycerol excess was eliminated by evaporation under reduced pressure and further purification was performed by gel filtration. The results are shown in Table 3.

TABLE 3

Glycosylation reaction with glycerol
(Standard reaction conditions: undried starch 1 g, glycerol 2.7 g)

| Compound | Temperature °C. | Time h | HCl Mol/L | Yield % | DP | % non substituted red. end |
|---|---|---|---|---|---|---|
| 5* | 80 | 2 | 1.27 | n.d. | 8.5 | 9.8 |
| 6** | 100 | 2 | 1.27 | 96 | 1.4 | 4.8 |
| 7 | 100 | 2 | 1.27 | n.d. | 4.7 | 0 |
| 8 | 100 | 2 | 2.54 | 77.1 | 1.6 | 10.4 |
| 9 | 100 | 2 | 5.08 | 87.7 | 1.7 | 28.2 |
| 10 | 100 | 2 | 5.08 | 81.9 | 2.0 | 26.8 |
| 11 | 100 | 2 | 5.08 | 79.3 | 2.1 | 25.7 |
| 12 | 100 | 4 | 1.27 | 98 | 1.5 | 6.4 |
| 13 | 100 | 4 | 5.08 | 95.8 | 1.2 | 19.2 |
| 14 | 100 | 4 | 5.08 | 85.7 | 1.2 | 20.9 |
| 15 | 100 | 16 | 1.27 | 99.3 | 1.4 | 0 |
| 16*** | 100 | 16 | 1.27 | 93.1 | 1.2 | 0 |
| 17 | 100 | 16 | 5.08 | 78.9 | 1.0 | 13.4 |
| 18 | 100 | 16 | 5.08 | 79.6 | 1.0 | 0 |
| 19 | 100 | 24 | 5.08 | 82.1 | 1.0 | 4.6 |
| 20 | 60 | 16 | 1.27 | n.d. | 1.35 | 17.1 |
| 21 | 60 | 16 | 1.27 | n.d. | 1.10 | 23.9 |
| 22 | 80 | 16 | 0.32 | 88.7 | 1.11 | 13.9 |
| 23 | 80 | 16 | 0.32 | 79.4 | 1.10 | 11.3 |
| 24 | 80 | 16 | 0.32 | 89.1 | 1.15 | 10.6 |
| 25 | 80 | 16 | 0.64 | 94.2 | 1.04 | 17.9 |
| 26 | 80 | 16 | 0.64 | n.d. | 1.03 | 21.7 |
| 27 | 80 | 16 | 0.64 | n.d. | 1.10 | 9.7 |
| 28 | 80 | 16 | 1.27 | n.d. | 1.03 | 11.4 |
| 29 | 80 | 16 | 1.27 | 99.8 | 1.01 | 8.6 |
| 30 | 80 | 16 | 1.27 | n.d. | 1.01 | 4.9 |

*Reaction conditions: starch 200 mg, glycerol 540 mg
**Reaction conditions: starch 600 mg, glycerol 1.62 g
***Reaction conditions: dry starch 1 g, glycerol 2.7 g The $^{13}C$ NMR spectrum of the completely depolymerized product and of one with a degree of polymerization of 4.7 are shown in FIG. 2. It is possible to observe the glycosidic anomeric signals α (100.9 ppm) and β (105.1 ppm), the $CH_2$ signals of both substituted (α=71.3 ppm, β=73 ppm) and non substituted (65.3 ppm) primary hydroxyl groups of glycerol, the CH signals (α=81.5 ppm, β–83 ppm) of secondary substituted hydroxyl group of glycerol.

The stability of one product shown in Table 3 was tested for stability under sterilization conditions and the observed variation at 284 nm is compared with that of glucose and methyl glycoside.

TABLE 4

Absorbance (284 nm) variation after sterilization (121° C. 45 min) of glycerol derivative and methyl glycoside

| Sample | % (w/v) | number of experiments | ΔAbs neutra (pH 6.5–7.5) | ΔAbs acid (pH 5.5) |
|---|---|---|---|---|
| No. 6 | 5 | 4 | 0.46 ± 0.32 | 0.35 ± 0.15 |
| glucose | 5 | 3 | 2.43 ± 0.9 | n.d. |
| Methyl glycoside | 2.5 | 1 | 0.01 | n.d. |
| glucose | 2.5 | 1 | 0.07 | n.d. |

In an in vitro test predictive of the dialytic efficiency of the osmotic agents described above, small dialysis bags with Spectra Pore membrane with a cut-off 500 Dalton (diameter 15 mm, 15 cm high) were filled with 3 ml of water solutions at different concentrations (2.5, 5.0% w/v of the samples). The bags were immersed in 200 ml of distilled water and 37° C. while stirring the extra dialysis solution. At given times (0, 1, 2, 3, 4, 5, 6 hours), the increase in the volume inside the dialysis bag was evaluated by weight and expressed as a percentage increase compared to the starting volume (Δw %). The mean results are shown in Table 5 and are compared with the results for glucose and glucose-1-phosphate.

TABLE 5

Volume increase in vitro dialysis test of modified icodextrins

| Samples | Moles/L | N of experiments | Δw % 1 h | Δw % 2 h | Δw % 3 h | Δw % 4 h | Δw % 5 h | Δw % 6 h |
|---|---|---|---|---|---|---|---|---|
| LMW red | 0.071 | 5 | 29.9 | 43.0 | 53.8 | 66.2 | 76.7 | 88.3 |
| LMW ox | n.d. | 5 | 20.2 | 29.2 | 39.3 | 46.0 | 56.4 | 63.4 |
| HMW1 red | 0.016 | 3 | 50.8 | 67.4 | 74.7 | 81.5 | 85.7 | 91.2 |
| HMW1 ox | n.d. | 3 | 22.8 | 43.3 | 60.2 | 77.0 | 89.6 | 104.2 |
| HMW2 red | 0.049 | 3 | 6.7 | 10.0 | 15.7 | 19.2 | 21.2 | 26.3 |
| HMW2 ox | n.d. | 4 | 32.2 | 52.9 | 69.7 | 84.2 | 96.0 | 106.4 |
| No. 6 (5%) | 0.215 | 1 | 33.2 | 68.2 | 98.1 | 119.5 | 140.5 | 159.8 |
| α-methyl-gluc. (5%) | 0.257 | 1 | 30.9 | 60.7 | 86.5 | 107.9 | 123.2 | 142.0 |
| β-methyl-gluc. (5%) | 0.257 | 1 | 45 | 76.1 | 103.0 | 129.7 | 151.7 | 174.9 |
| No. 6 (2.5%) | 0.108 | 2 | 22.9 | 34.4 | 50.0 | 63.0 | 77.2 | 87.7 |
| α-methyl-gluc. (2.5%) | 0.128 | 3 | 21.8 | 39.2 | 55.4 | 67.64 | 79.5 | 92.1 |
| β-methyl-gluc. (2.5%) | 0.128 | 3 | 34.0 | 50.3 | 63.7 | 67.6 | 77.7 | 86.5 |
| glucose (2.5%) | 0.138 | 3 | 15.3 | 34.2 | 43.4 | 57.3 | 74.2 | 90.9 |
| gluc.-1-phos. (2.5%) | 0.069 | 3 | 35.8 | 53.6 | 76.3 | 95.9 | 120.1 | 144.1 |

Accordingly, the present invention provides a number of heat stable osmotic agents that provide a suitable substitute for glucose, improved peritoneal dialysis solutions containing stable osmotic agents as well as a variety of methods of producing improved peritoneal dialysis solutions.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. A method of preparing a stabilized osmotic agent solution comprising the following step:
   dissolving starch in an acid and an alcohol selected from the group consisting of methanol, butanol and glycerol.

2. The method of claim 1 further comprising the step of stirring the starch, alcohol and acid for about 2 hours.

3. The method of claim 1 wherein the stirring step is carried out at a temperature of about 100° C.

4. The method of claim 1 wherein the starch is maltodextrin.

5. The method of claim 1 wherein the acid is HCl.

6. The method of claim 1 wherein the starch is glycosylated to an icodextrin linked predominately by α-1,4 bonds and having the formula:

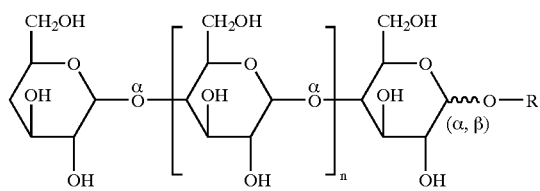

wherein R is selected from the group consisting of $CH_3$, $CH_3CH_2$ and $(CH_2OH)_2CH$.

* * * * *